United States Patent [19]

Meistrell

[11] Patent Number: 4,805,620
[45] Date of Patent: Feb. 21, 1989

[54] ADJUSTABLE WRAPPABLE, STRETCHABLE WRAP SHEET

[75] Inventor: William R. Meistrell, Manhattan Beach, Calif.

[73] Assignee: Dive N'Surf, Inc., Hermosa Beach, Calif.

[21] Appl. No.: 61,810

[22] Filed: Jun. 15, 1987

Related U.S. Application Data

[63] Continuation-in-part of Ser. No. 803,634, Dec. 2, 1985, Pat. No. 4,706,673, which is a continuation-in-part of Ser. No. 687,909, Dec. 31, 1984, Pat. No. 4,585,003.

[51] Int. Cl.$^4$ ............................ A61F 7/00; A61N 3/00
[52] U.S. Cl. ................................. 128/402; 128/403; 128/379; 383/907
[58] Field of Search ............... 128/384, 402, 403, 399, 128/380, 379, DIG. 15, 82.1, 94; 383/401; 62/530; 219/527; 165/46

[56] References Cited

U.S. PATENT DOCUMENTS

| | | | |
|---|---|---|---|
| 1,736,590 | 11/1929 | Graham et al. | 128/384 |
| 3,092,110 | 6/1963 | Duemsing | 128/402 |
| 3,491,761 | 1/1970 | Baker | 128/403 |
| 4,381,025 | 4/1983 | Schooley | 128/402 |
| 4,534,354 | 8/1985 | Bommer Jr. et al. | 128/402 |
| 4,585,003 | 4/1986 | Meistrell | 128/402 |
| 4,706,673 | 11/1987 | Meistrell | 128/402 |

OTHER PUBLICATIONS

Therm-O-Rite; from "Surgery" Magazine Apr. 1965, vol. 57 #4 pg. 19 (Advertisement).

Primary Examiner—Richard C. Pinkham
Assistant Examiner—Mark S. Graham
Attorney, Agent, or Firm—William W. Haefliger

[57] ABSTRACT

A wrap sheet, for compressively wrapping a user's anatomy, such as a joint, comprising an insulative, flexible, relatively thin sheet that is bi-directionally stretchable, the sheet including a first elastomeric layer, and a second layer of pile fabric attached to and substantially covering one side of the first layer; the sheet is adapted to be adjustably wrapped, and tensioned about a user's anatomy; and there are hook elements carried by the sheet for removably attaching to the second layer at any position of wrap adjustment of the sheet. A hot or cold pack may be integrated with the sheet, for retention by the wrap against the user's anatomy.

6 Claims, 3 Drawing Sheets

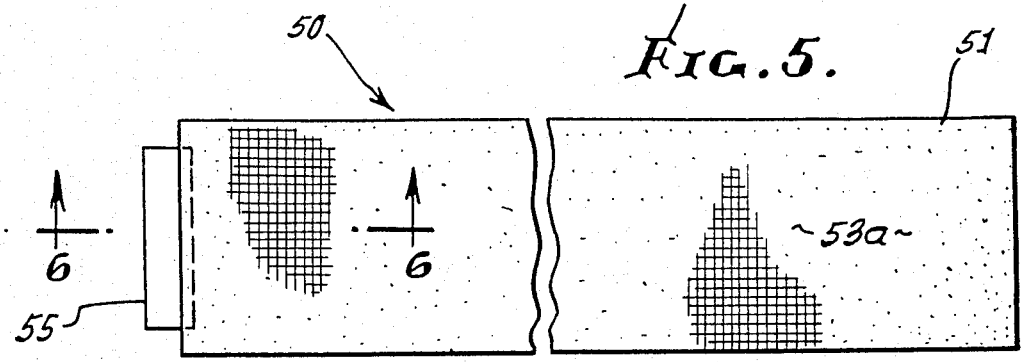
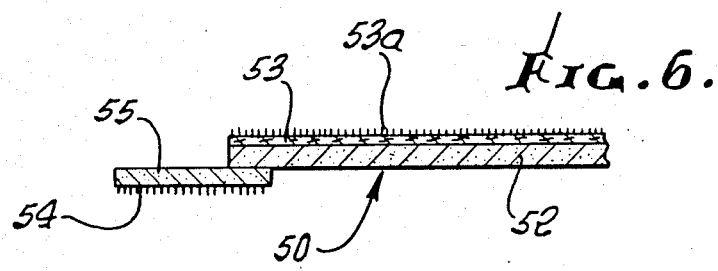
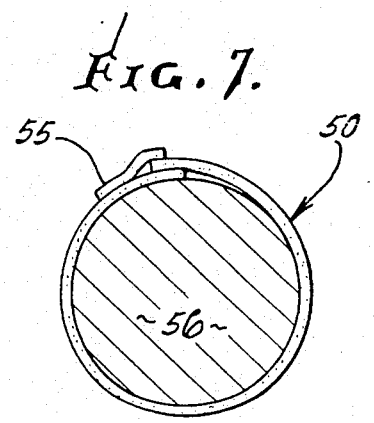
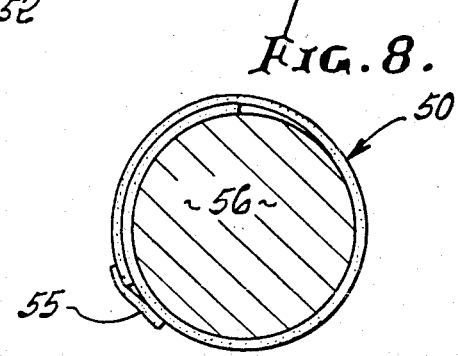
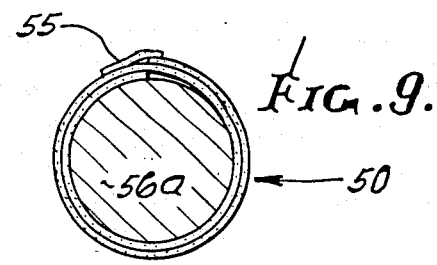
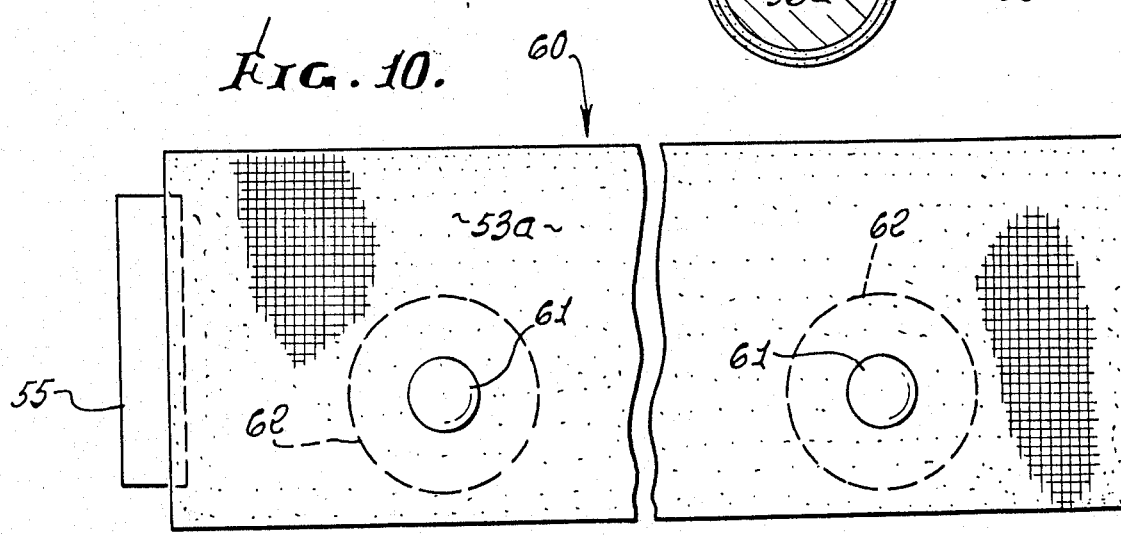

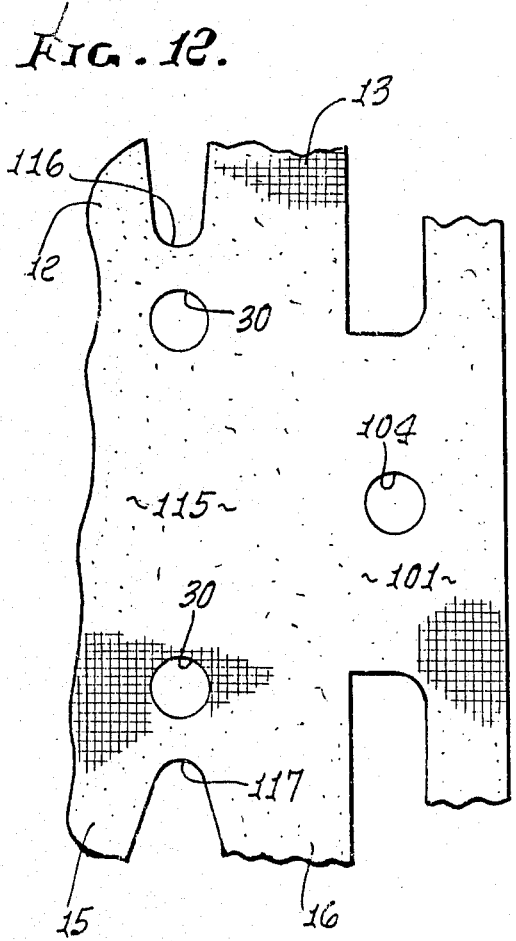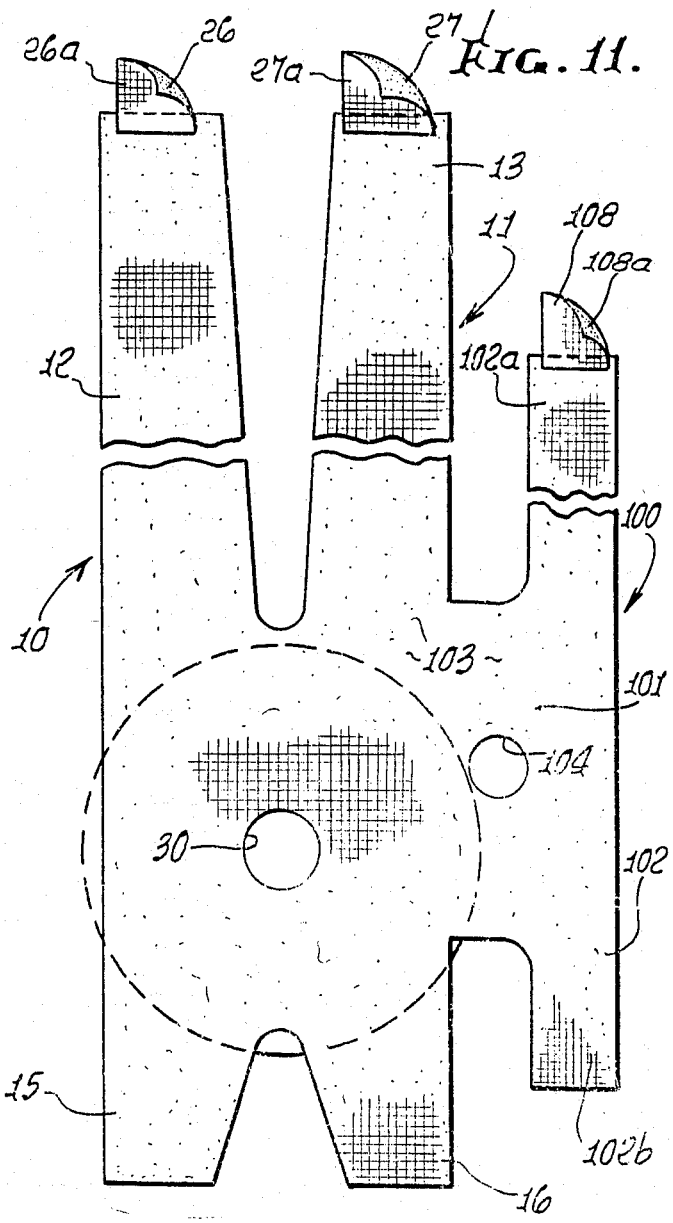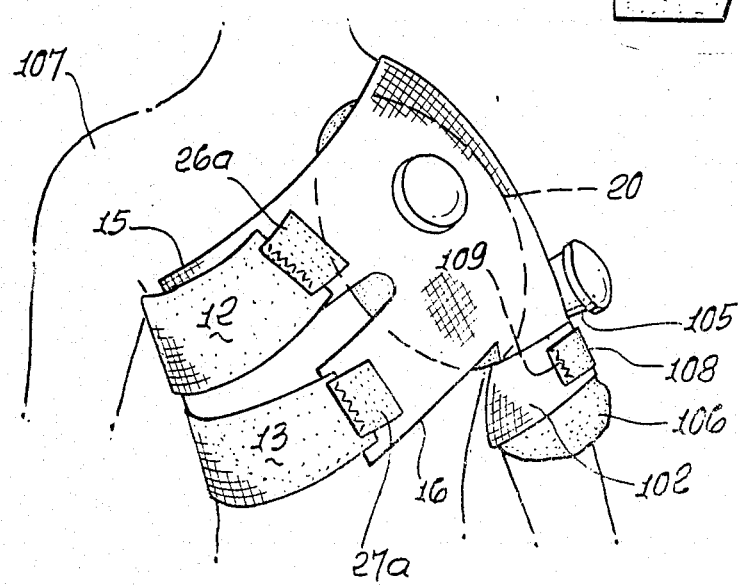

ADJUSTABLE WRAPPABLE, STRETCHABLE WRAP SHEET

BACKGROUND OF THE INVENTION

This application is a continuation-in-part of Ser. No. 803,634, filed Dec. 2, 1985, now U.S. Pat. No. 4,706,673, which is a continuation-in-part of Ser. No. 687,909, filed Dec. 31, 1984, now U.S. Pat. No. 4,585,003. This invention relates generally to stretchable wrap sheets which are adjustable; and more particularly concerns an improved device which is adjustably wrappable through a wide range of wrap sizes, and easily attaches to the body of the user, as for example to his knee joint region or elbow joint region, and at the same time allows flexibility of the joint, as during walking, and may be used for holding cold or hot packs in place.

There is need for means to quickly and adjustably wrap about body joints, limbs, etc., characterized by a wide range of wrap sizes, and for means to adequately hold cold or hot packs in place on the bodies of users; and this need is critical as respects user's limbs which are required to flex, in use.

SUMMARY OF THE INVENTION

It is a major object of the invention to provide an apparatus meeting the above need, and which also provides additional advantages such as ease of attachment, ease of detachment; blockage of heat transfer from the pack to the exterior (i.e. away from the user's body), and blockage of heat transfer from the exterior to the pack, while it is retained in position; and flexibility and stretchability of the sheet, to best conform to the in-place pack as well the user's body to which it is wrapped or retained, in use. Basically, the device comprises:

(a) an insulative, flexible, relatively thin sheet that is bi-directionally stretchable, the sheet including a first elastomeric layer, and a second layer of pile fabric attached to and substantially covering one side of the first layer, (b) the sheet adapted to be adjustably wrapped and to be adjustably tensioned, about a user's anatomy, and there being hook elements carried by the sheet to removably attach to said second layer at any position of wrap adjustment of the sheet.

As will appear, the sheet preferably has stretchability, and is in at least partly stretched condition in use, conforming to the shifting position of the user's body (such as a limb), allowing the user to walk about with his joint compressively wrapped or to flex his wrapped arm, and the wrap easily affords different degrees of compression exertion on the body.

It is a further object of the invention to provide an improved device of the above character, wherein the thin sheet comprises an insulative, flexible, stretchable layer of material such as elastomer, foamed rubber being usable, and pile fabric covering one side of the elastomer layer, to allow a wide range of attachment points for hook tab means carried by the sheet.

It is further object of the invention to provide an anchor for the pack, as for example a hole or holes in the main portion of the sheet, as will appear.

Finally, it is an object of the invention to provide a single device to hold multiple hot or cold packs, as adjacent the upper chest and upper arm of the human wearer.

These and other objects and advantages of the invention, as well as the details of illustrative embodiments, will be more fully understood from the following specification and drawings, in which:

DRAWING DESCRIPTION

FIG. 5 is a plan view of a modified wrap;

FIG. 6 is an enlarged fragmentary section taken on lines 6—6 of FIG. 5;

FIG. 7 and 8 are cross sections showing different extents of stretchable wrapping and compression exertions;

FIG. 9 is a view like FIG. 7, showing another use of the wrap;

FIG. 10 is a plan view of yet another modified wrap;

FIG. 11 is like FIG. 1, and shows a modified device;

FIG. 12 is like FIG. 11, and shows a further modification; and

FIG. 13 is a view showing application of the FIG. 11 device to a human wearer.

DETAILED DESCRIPTION

Figure 3:
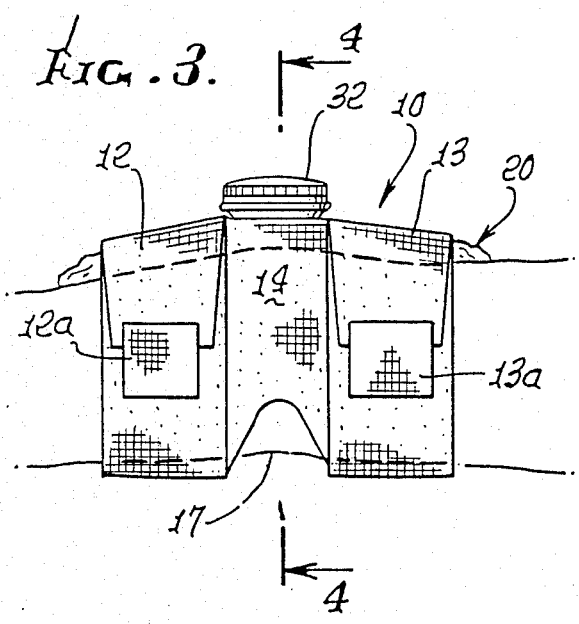
FIG. 3 is a side elevational view showing the sheet wrapped about the knee of a user.
Figure 4:
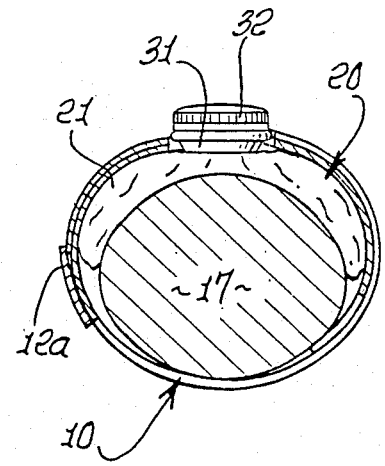
FIG. 4 is a section on lines 4—4 of FIG. 3.

In the drawings, the hot or cold pack retention device 10 comprises an elongated, insulative, flexible, relatively thin sheet 11 having two generally parallel elongated legs 12 and 13 joined to a sheet main portion 14. The latter may have oppositely extending stub legs 15 and 16, as shown, to be covered by the legs 12 and 13, during wrapping, as in FIGS. 3 and 4. The sheet is preferably stretchable to conform closely to the hot pack 20 positioned over the body extent (such as a knee 17, or elbow joint or neck) for comfortably holding the pack in such position during flexing of the joint, or body, as during walking or arm flexing. In this regard, the pack 20 may consist of a flexible bag 21 containing cold or warm water, and may contain ice pieces. The bag tubular neck 31 is typically rigid, and mounts a removable cap 32.

Figure 1:
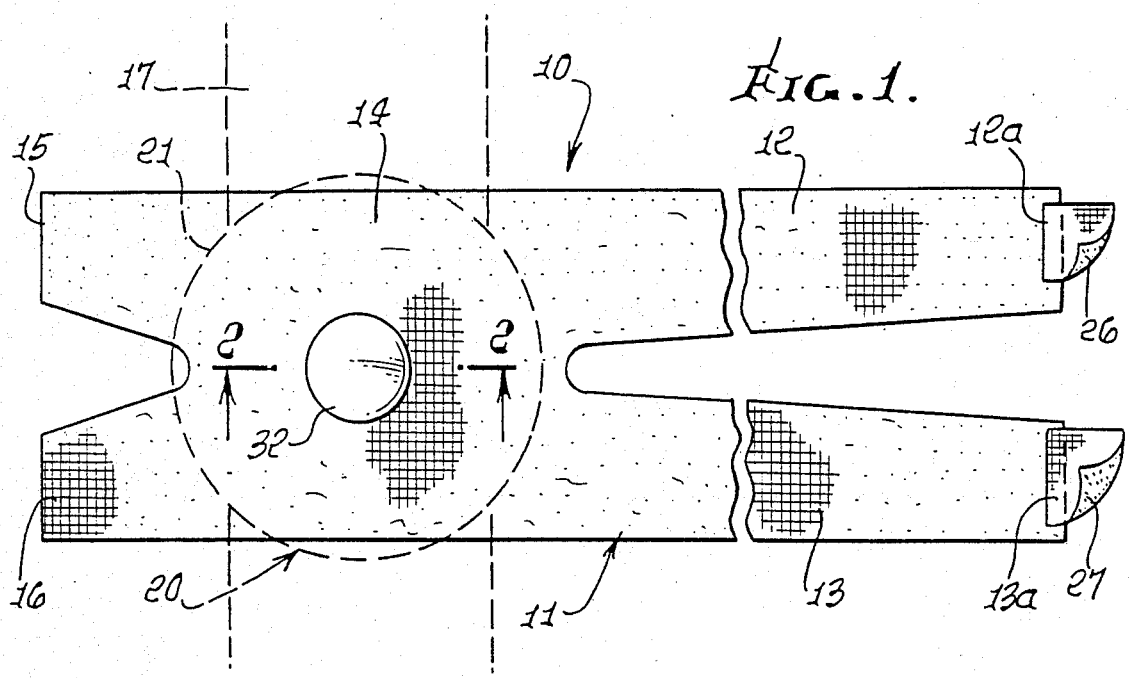
FIG. 1 is a top plan view of a wrap-type retention device incorporating the invention.
Figure 2:
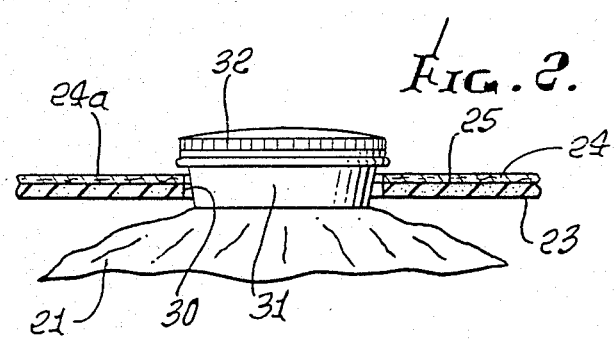
FIG. 2 is a section on lines 2—2 of FIG. 1.

The sheet main portion 14 is provided with an anchor to anchor the pack in position when the sheet main portion is placed over the joint, as is seen in FIG. 1. Note that the sheet main portion is sized to substantially cover and grip the bag, when the latter is partially flattened, as in FIG. 3, with liquid therein. The bag is gripped for example due to the fact that the sheet includes or comprises an underlayer 23 of elastomer, such as foamed rubber (NEOPRENE) of a thickness between 1/32 and ¼ inch. Such material is stretchable bi-directionally (in all directions) to best conform to the user's flexing joint and to the shifting position of the bag liquid contents, while tensioned, in use.

Attached to the layer 23 (as by adhesive at 25) is an upper or outer layer 24 of fabric having outward facing hook or pile element construction, to attach to pile or hook elements, respectively proximate the ends of the legs, during wrapping. Such elements are indicated at 26 and 27 at the underside of the leg extension 12a and 13a, in FIG. 1, and they removably attach, as by finger pressure, to any portion of the outer surface 24a of the layer 24, during wrap-up. Accordingly, the leg extension may be positioned anywhere over the surface 24a of layer 24 on legs 12 or 13, or the main portion 14 of the body, for maximum comfort and adjustably, and in conformance with retention of the bag 21 in curved or other position, over the body joint, or body surface.

The anchor may be generally centrally located on main body portion 14, and may with unusual advantage comprise a through opening or hole 30 through portion 14, sized to loosely, i.e. fittingly receive the tubular neck 31 of the bag 21, slipped through the opening. A cap 32 is shown on the neck, and is removable to change the liquid contents of the bag. Legs 12 and 13 wrap over the pack 20, at opposite sides of the neck and cap, to leave it exposed for such liquid change; at the same time, the sheet is anchored to the neck, as described, and the bag is comfortably retained in position on the ailing or bruised joint, the legs 12 and 13 being slightly tensioned.

Removal of the wrap is very simple, to allow complete removal of the bag 21, as described, and subsequent replacement. It will be noted that the sheet is insulative, to block heat access from the exterior to the bag, in the case of a cold pack, and to block heat escape to the exterior (i.e. away from the joint), in the case of a hot pack.

The sheet 11 may consist of the commercial product known as STARSKIN, 3 mm #1 smooth skin plush royal 403, produced by St. Albans Rubber Ltd., St. Albans, Herts, England.

In FIGS. 5 and 6, the wrap 50 for a user's anatomy includes an insulative, flexible, relatively thin, elongated sheet 51 that is bi-directionally stretchable. It includes a first (inner elastomeric layer 52 corresponding to layer 23, and a second and thinner (outer) layer of fabric 53 having outward facing hook or pile construction 53a (preferably pile) to attach to pile or hook elements (preferably hooks) 54 as on tabs 55 carried by the sheet, as at one end thereof. Layer 52 is bonded to the fabric 53. Preferably the pile construction covers or substantially covers or extends throughout the major length of layer 52.

Such construction enables great versatility or adjustability of the wrap, both as to exertion of a wide range of compressive forces, and use of the same wrap on a wide range of joint or limb sizes. Thus, as shown in FIG. 7, the wrap extends over limb 56, and extends about 370° about the limb; in FIG. 8, the same wrap has been stretched about the same limb to extend about 470° about the limb, to exert greater compression on the limb or joint; and in FIG. 9, the same wrap extends about a smaller limb 56a, wrapped about 720° about that limb. This is made possible because the hooks on tab 55 may attach anywhere on the outer pile surface of the wrap.

FIG. 10 shows a modified and elongated wrap 60, having greater width than that of FIG. 5; however its construction is the same as shown in FIG. 6. Two holes are formed through the wrap (corresponding to holes 30 in FIG. 1), to receive the necks 61 of two hot or cold packs 62. (The latter may for example be spaced to be applied to the hips of an injured athlete). As before, the hook elements 54 on tab 54 are attachable anywhere on the pile surface 53a of fabric layer 53, which extends throughout or substantially throughout the length and width of the rectangular elastomer layer 52.

The device of FIG. 11 is in part like that of FIG. 1, that part bearing the same numerals. In addition, the sheet includes a T-shaped portion 100 having a stem 101 and a cross-piece 102, of the same material as sheet 11. Stem 101 is integral with the mid-portion 103 of sheet 11, and projects laterally. The cross-piece 102 projects longitudinally and has oppositely extending legs 102a and 102b spaced from the main sheet 11. The T-shaped portion, and in particular the stem 101, form an additional through opening 104 to receive the neck 105 of an additional hot or cold liquid pack 106 applicable to the upper arm of a human wearer 107, as seen in FIG. 13.

Additional tab means 108 is integral with one end of the cross-piece, i.e. leg 102a in the example. That tab may contact the first elastomer layer and the leg 102a and be stitched thereto at 109. See corresponding stitches attaching tabs 26 and 27 to legs 12 and 13. Tab 108 carries hook elements 108a to removably attach to pile 111 on leg 102b, or anywhere on the cross-piece when the cross-piece legs are wrapped about the upper arm of the wearer as in FIG. 13. At that time, tabs 26a and 27a removably attach (hook and pile connection) to the first sheet surface as seen in FIG. 13, so that hot or cold pack 20 engages the upper chest area of the wearer. The sheet 11 wraps about the wearer's shoulder and across his chest and back, and then at the opposite side of his torso, below his other arm, as shown. Stretchability, bi-directionally of the sheet and T-shaped portion, plus ability of the tabs to connect to any surface portion of the sheet and T-shaped section, facilitate comfortable, close fitting for the wearer, to hold the packs in position during ambulatory movement of the wearer.

FIG. 12 is like FIG. 11, except for the provision of two holes 30 in the sheet mid-portion 115, between U-shaped inner terminals 116 and 117 of the legs 12 and 13, and 15 and 16. Holes 30 are sized to fit the necks of two packs, as described.

The two adjustably tightenable wrap connections (about the shoulder and torso, and about the upper arm), connected by the stem 101, stably support the liquid packs in otherwise inherently unstable positions.

I claim:

1. In a retention device for use with a hot or cold liquid pack, the pack having a neck, the device itself comprising
   (a) an insulative, flexible, relatively thin sheet that is longitudinally elongated and is bi-directional stretchable lonitudinally and laterally, the sheet including a first elastomeric layer, consisting of neoprene foam and a second layer of pile fabric attached to and substantially covering one side of the first layer,
   (b) the sheet having a portion forming a first through opening to receive said pack neck and said portion then substantially flatly engaging the pack extent about said neck, the opening surrounded by pile fabric,
   (c) the remainder of the sheet then adapted to adjustably wrap, and to be tensioned, about a user's anatomy, and there being first tab means integral with and contacting said first elastomer layer at one end portion of the sheet, the tab means carrying hook elements for removably attaching to said second layer at any position of wrap adjustment of the sheet,
   (d) the sheet having a mid-portion in which said opening is formed, and the sheet also including a T-shaped portion defining a stem and a cross-piece, the stem projecting laterally from and substantially in the plane of said mid-portion and said cross-piece extending longitudinally beyond the stem in laterally openly spaced relation from the main extent of the sheet, the T-shaped portion forming a second through opening to receive the neck of an auxiliary hot or cold liquid pack, (e) the cross-piece having an overall length less than that of the main extent of the sheet, (f) and including additional tab means integral with one end of said cross-piece, the additional tab means carrying hook elements for removably attaching to said second layer on the T-shaped section at any position of wrap adjustment of the cross-piece about the upper arm of a human wearer, and when the sheet mid-portion extends over the shoulder of the wearer.

2. The device of claim 1 including said pack having its neck projecting in said first through opening.

3. The device of claim 2 wherein said pack includes a flexible bag which is at least partly flattened and sidewardly engaged by said elastomer layer.

4. The device of claim 1 wherein the sheet is elongated to have opposite ends, each of which is bifurcated, and said first tab means is attached to legs defined by one of said sheet bifurcated ends.

5. The device of claim 1 wherein said additional through opening is formed in the stem of said T-shaped portion.

6. The device of claim 1 including first and second liquid packs with their necks received in said first and second openings so that the packs are positioned to extend adjacent the upper chest and the upper arm, respectively, of the wearer.

* * * * *